United States Patent [19]

Gay et al.

[11] Patent Number: 5,200,444
[45] Date of Patent: Apr. 6, 1993

[54] POLYMER MATRICES HEAT AND LIGHT STABILIZED WITH NOVEL BENZOPHENONE/1,4-DIHYDROPYRIDINE COMPOUNDS

[75] Inventors: Michel Gay, Villeurbanne; Sylvie Lavault, Lyons, both of France

[73] Assignee: Rhone-Poulenc Chimie, Courbevoie, France

[21] Appl. No.: 626,767

[22] Filed: Dec. 13, 1990

Related U.S. Application Data

[62] Division of Ser. No. 531,296, May 31, 1990, Pat. No. 5,034,533.

[30] Foreign Application Priority Data

May 31, 1989 [FR] France .................. 89 07415

[51] Int. Cl.$^5$ .................................. C08K 5/34
[52] U.S. Cl. ...................... 524/99; 524/400; 524/443
[58] Field of Search .................. 524/99, 400, 443

[56] References Cited

U.S. PATENT DOCUMENTS 5,034,533  7/1991  Gay et al. .................. 546/321

*Primary Examiner*—Kriellion S. Morgan
*Attorney, Agent, or Firm*—Burns, Doane, Swecker & Mathis

[57] ABSTRACT

Polymer matrices, e.g., halogenated polymers such as PVC, polyolefins, polystyrenes, polyalkadienes, etc., are stabilized against the adverse effects of heat and light, by incorporating therein an effective stabilizing amount of a compound of the formula (I):

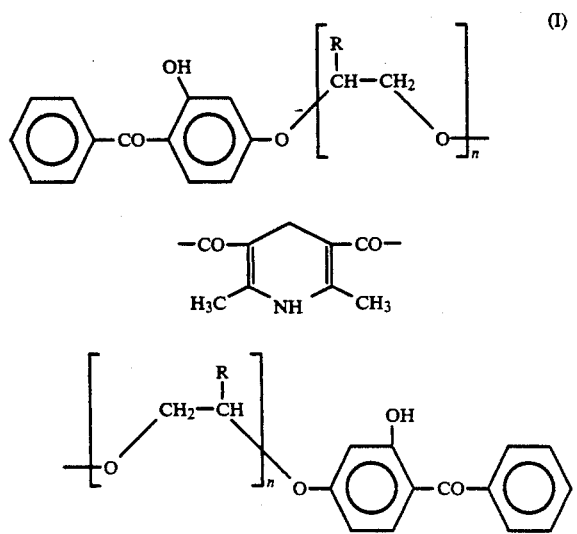

in which n is a number ranging from 1 to 3, and R is a methyl radical or a hydrogen atom.

15 Claims, No Drawings

POLYMER MATRICES HEAT AND LIGHT STABILIZED WITH NOVEL BENZOPHENONE/1,4-DIHYDROPYRIDINE COMPOUNDS

This application is a division of application Ser. No. 07/531,296, filed May 31, 1990, now U.S. Pat. No. 5,034,533.

BACKGROUND OF THE INVENTION

1. Field of the Invention

The present invention relates to novel compounds comprising a dihydropyridine basic nucleus and to the use of such novel compounds for the heat and light stabilization of a wide variety of polymers, notably PVC.

2. Description of the Prior Art

FR-A-2,239,496 describes 2,6-dimethyl-3,5-dicarboxylate-1,4-dihydropyridines as heat stabilizers for polyvinyl chloride (PVC).

EP-A-0,005,678 describes a synergistic composition of 2,6-dimethyl-3,5-dicarboxylate-1,4-dihydropyridines and β-diketones for the heat stabilization of PVC.

The above 1,4-dihydropyridine compounds are highly effective for the heat stabilization of PVC. However, they are inadequate for certain applications where the polymer is subjected to outdoor exposures, i.e., when it is necessary to also have stability to light.

SUMMARY OF THE INVENTION

Accordingly, a major object of the present invention is the provision of novel compounds that can be used for both the heat and light stabilization of a wide variety of polymers, notably PVC, which novel compounds include a 1,4-dihydropyridine basic nucleus and have the structural formula (I):

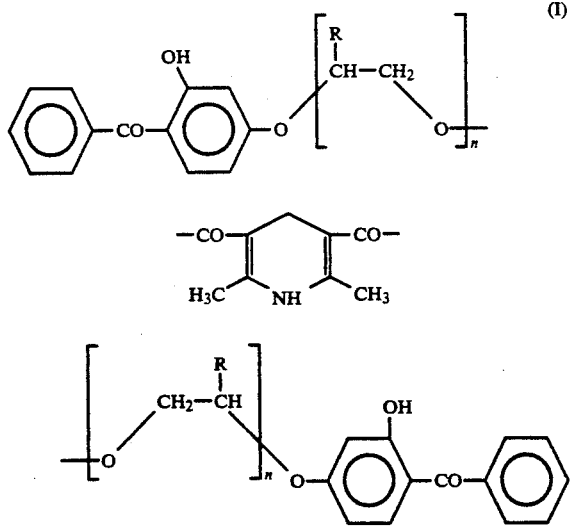

in which n is a number ranging from 1 to 3, and R is a methyl radical or a hydrogen atom.

DETAILED DESCRIPTION OF THE PREFERRED EMBODIMENTS OF THE INVENTION

More particularly according to the present invention, the compounds of formula (I) are prepared from 2-hydroxy-4-hydroxyalkoxybenzophenone (or 2-hydroxy-4-hydroxy-(polyalkoxy)benzophenone) and diketene to form the corresponding acetoacetate of the substituted benzophenone.

The acetoacetate thus obtained is then reacted with ammonium acetate in the presence of hexamethylenetetramine according to a process per se known to this art which enables 2,6-dimethyl-3,5-dicarboxylate-1,4-dihydropyridines to be prepared from the corresponding acetoacetates.

More generally, the compounds of formula (I) are prepared according to Hantzch's method, in two stages:

(1) reaction of formaldehyde with the acetoacetate, producing the methylenebisacetoacetate of the substituted benzophenone; and (2) ring closure of this latter compound to the corresponding 1,4-dihydropyridine, using ammonia.

It is also possible, by reversing the above two stages, to react formaldehyde with the β-aminocrotonate derived from the acetoacetate.

Among the compounds of formula (I), the more preferred are those in which n=1, namely:

(i) 3,5-bis[2-(4-benzoyl-3-hydroxyphenoxy)ethoxycarbonyl]-2,6-dimethyl-1,4-dihydropyridine; and (ii) 3,5-bis[2-(4-benzoyl-3-hydroxyphenoxy)-2-methylethoxycarbonyl]-2,6-dimethyl-1,4-dihydropyridine.

The compounds of formula (I) can be used as heat and light stabilizers for diverse organic polymers.

They can thus be employed in halogenated polymers and especially in chlorinated polymers. They exert a heat-stabilizing effect on these polymers and also an effect of protection against light and in particular against ultraviolet (UV) radiations. They can be used either alone or in combination with other heat stabilizers such as, for example, organic tin derivatives.

The compounds of the invention are also advantageously used in chlorinated polymers in combination with other primary heat stabilizers.

These primary stabilizers are preferably organic zinc, calcium, barium, magnesium and strontium derivatives and, if appropriate, hydrotalcites.

Thus, the present invention also features compositions based on stabilized chlorinated polymers and which comprise:

(a) an effective amount of at least one organic zinc compound;

(b) an effective amount of at least one organic calcium, barium, magnesium or strontium compound and/or of a hydrotalcite;

(c) an effective amount of at least one 1,4-dihydropyridine compound having the formula (I).

The chlorinated polymers are advantageously polyvinyl chloride (PVC), polyvinylidene chloride, copolymers comprising predominantly vinyl chloride recurring units derived from vinyl chloride and other monomers, and mixtures of polymers or copolymers in which a predominant fraction is obtained from vinyl chloride.

In general, PVC of any type is suitable, whatever the method of its preparation: polymerization in bulk, in suspension, in dispersion or of any other type, and whatever its intrinsic viscosity.

The vinyl chloride homopolymers may also be modified chemically, for example by chlorination.

Many vinyl chloride copolymers can also be stabilized against the effects of heat, namely, yellowing and degradation. These are, in particular, the copolymers obtained by copolymerization of vinyl chloride with other monomers containing a polymerizable ethylenic bond, such as, for example, vinyl acetate or vinylidene chloride, maleic or fumaric acids or their esters, olefins such as ethylene, propylene or hexene, acrylic or methacrylic esters, styrene, and vinyl ethers such as vinyl dodecyl ether.

These copolymers typically contain at least 50% by weight of vinyl chloride recurring units and preferably at least 80% by weight of vinyl chloride recurring units.

The compositions according to the invention may also contain mixtures based on chlorinated polymer containing minor amounts of other polymers, such as halogenated polyolefins or acrylonitrile/butadiene/styrene (ABS) copolymers.

PVC by itself or mixed with other polymers is the chlorinated polymer most typically employed in the compositions of the invention.

The organic zinc compounds are preferably zinc carboxylates and phenolates.

Those most advantageously used are, for example, zinc salts of maleic, acetic, diacetic, propionic, hexanoic, 2-ethylhexanoic, decanoic, undecanoic, lauric, myristic, palmitic, stearic, oleic, ricinoleic, behenic, hydroxystearic, hydroxyundecanoic, benzoic, phenylacetic, para-tert-butylbenzoic and salicylic acids, and zinc phenolates of phenol and of phenols substituted by one or more alkyl radicals, such as nonylphenols.

For practical or for economic reasons, the preferred organic zinc compounds referred to above are zinc propionate, zinc 2-ethylhexanoate, zinc laurate, zinc stearate, zinc oleate, zinc ricinoleate, zinc benzoate, zinc para-tert-butylbenzoate, zinc salicylate, zinc mono(2-ethylhexyl) maleate and zinc nonylphenates.

The organic zinc compounds advantageously are present in an amount ranging from 0.005% to 1% by weight relative to the chlorinated polymer, and preferably from 0.01% to 0.6% by weight.

The organic calcium, barium, magnesium and strontium compounds are preferably the carboxylates and the phenolates of these metals.

Those most advantageously used are, for example, the calcium, barium, magnesium and strontium salts of maleic, acetic, diacetic, propionic, hexanoic, 2-ethylhexanoic, decanoic, undecanoic, lauric, myristic, palmitic, stearic, oleic, ricinoleic, behenic, hydroxystearic, hydroxyundecanoic, benzoic, phenylacetic, para-tert-butylbenzoic and salicylic acids, and calcium, barium, magnesium and strontium phenolates of phenol and of phenols substituted by one or more alkyl radicals, such as nonylphenols.

For practical or for economic reasons, the preferred organic calcium, barium, magnesium and strontium compounds referred to above the calcium, barium and magnesium salts of propionic, 2-ethylhexanoic, lauric, stearic, oleic, ricinoleic, benzoic, para-tert-butylbenzoic and salicylic acids, of mono(2-ethylhexyl)maleate, and calcium, barium and magnesium nonylphenates.

The organic calcium, barium, magnesium and strontium compounds or hydrotalcites advantageously are present in an amount ranging from 0.005% to 5% by weight relative to the chlorinated polymer, and preferably from 0.02% to 2% by weight.

For food-contact applications and especially in the case of PVC bottles, organic calcium compounds or mixtures of organic calcium compounds and organic magnesium compounds will be employed.

The hydrotalcites which may be introduced into the compositions based on a chlorinated polymer according to the invention instead of the organic calcium, barium, magnesium and strontium compounds or together with these compounds, are especially the compounds which have been described in FR-A-2,483,934 and in EP-A-0,063,180.

The compositions based on chlorinated polymer typically contain from 0.005% to 5% by weight of compound of formula (I) relative to the chlorinated polymer.

They preferably contain from 0.01% to 2% by weight of compound of formula (I) relative to the chlorinated polymer.

When compared with the 1,4-dihydropyridines of the prior art, employed as heat stabilizers for chlorinated polymers, the compounds of formula (I) exhibit substantially the same effectiveness from the standpoint of heat stabilization for the same amount by weight thereof, namely, for a lesser amount of 1,4-dihydropyridine units, while additionally providing an efficient protective action against UV irradiation.

It is of course possible to introduce other additives as well into the compositions based on chlorinated polymer of the invention.

This is especially the case as regards the $\beta$-diketones or $\beta$-diketoaldehydes, which exhibit a synergistic effect in combination with compounds containing a dihydropyridine functional group.

Such $\beta$-diketones have been described, in particular, in FR 2,292,227, FR 2,324,681, FR 2,351,149, FR 2,352,025, FR 2,383,988 and FR 2,456,132 and in EP 0,040,286 and EP 0,046,161.

Exemplary such $\beta$-diketones include benzoylstearoylmethane, dibenzoylmethane, benzoylacetone, benzoyl-3-methylbutanoylmethane, methoxycarbonylbenzoylbenzoylmethanes, bis-$\beta$-diketones such as 1,4-bis(acetylaceto)butane, 1,8-bis-(benzoylaceto)octane and 1,4-bis(acetylaceto)benzene.

When present, the $\beta$-diketones constitute from 0.005% to 5% by weight relative to the chlorinated polymer, and preferably from 0.01% to 2% by weight.

The compositions of the invention may contain other secondary heat stabilizers, such as polyols, phosphites or epoxy compounds.

The polyols generally have the advantage of lengthening the lifetime of the chlorinated polymers subjected to a heat treatment.

It is generally preferably that the polyols employed have a boiling point higher than 150° C. and preferably higher than 170° C., because of the processing of the chlorinated polymers at elevated temperatures.

Exemplary such polyols include the triols such as trimethylolpropane, glycerol, 1,2,6-hexanetriol, 1,2,4-butanetriol or trishydroxyethyl isocyanurate, tetrols such as pentaerythritol or diglycerol, pentitols such as xylitol or tetramethylolcyclohexanol, hexitols such as mannitol, sorbitol or dipentaerythritol, polyols which are partially esterified with a carboxylic acid and in the formula of which at least 3 hydroxyl functional groups are free, polyvinyl alcohols, especially those in which there remain less than 30 mol % of ester groups relative to the total number of their ester and hydroxyl groups and which have a viscosity ranging from approximately $4 \times 10^{-3}$ Pa.s to $60 \times 10^{-3}$ Pa.s at 20° C. in an aqueous solution at a concentration of 4% by weight.

Among these polyols, those preferred are xylitol, mannitol, sorbitol, tetramethylolcyclohexanol and the polyvinyl alcohols described above.

When it is present in the compositions according to the invention, from 0.005% to 1% by weight of polyol is typically incorporated relative to the weight of the chlorinated polymer, and preferably from 0.01% to 0.6% by weight.

The epoxides which may be used in the compositions of this invention are generally complex compounds, typically epoxidized polyglycerides such as epoxidized soya oil, which is the most common, epoxidized linseed oil, epoxidized fish oils and epoxidized tallol.

The compositions according to the invention may also contain organic phosphites, especially aliphatic phosphites or aromatic phosphites, or mixed aliphatic and aromatic phosphites.

Particularly exemplary thereof are the following:

(i) Pentaerythrityl dialkyl diphosphites;

(ii) Pentaerythrityl diphenyl diphosphites;

(iii) Pentaerythrityl bis(2,4-di-tert-butylphenyl) diphosphites;

(iv) Tetraalkyl bis(1,4-phenylene)dimethylmethane diphosphites;

(v) Tetraalkyl bis(2,5-dialkyl-1,4-phenylene)alkylmethane diphosphites;

(vi) Diphenyl bis[2-(2-butoxyethoxy)ethyl]4,4'-isopropylidenediphenyl diphosphite;

(vii) Tetrakis[2-(2-butoxyethoxy)ethyl]4,4'-isopropylidenediphenyl diphosphite;

(viii) Diphenyl tris[2-(2-butoxyethoxy)ethyl]bis(4,4'-isopropylidenediphenyl) triphosphite;

(ix) Diphenyl tetrakis[2-(2-butoxyethoxy)ethyl]tris(4,4'-isopropylidenediphenyl) tetraphosphite;

(x) Diphenyl bis[2-(2-butoxyethoxy)ethyl]4,4'-isopropylidenediphenyl diphosphite;

(xi) Tetrakis[2-(2-butoxyethoxy)ethyl]-4,4'-isopropylidenediphenyl diphosphite;

(xii) Diphenyl tris[2-(2-butoxyethoxy)ethyl]bis(4,4'-isopropylidenediphenyl) triphosphite;

(xiii) Diphenyl tetrakis[2-(2-butoxyethoxy)ethyl]tris(4,4'-isopropylidenediphenyl) tetraphosphite; tetrakis(4,4'-isopropylidenediphenyl) pentaphosphite;

(xv) Diphenyl hexakis[2-(2-butoxyethoxy)ethyl]pentakis(4,4'-isopropylidenediphenyl) hexaphosphite;

(xvi) Pentakis[2-(2-butoxyethoxy)ethyl]bis(4,4'-isopropylidenediphenyl) triphosphite;

(xvii) Hexakis[2-(2-butoxyethoxy)ethyl]tris(4,4'-isopropylidenediphenyl) tetraphosphite;

(xviii) Bis(2,4-di-tert-butylphenyl) bis[2-(2-butoxyethoxy)ethyl]4,4'-isopropylidenediphenyl diphosphite; and (xix) Bis(2,6-di-tert-butylphenyl) bis[2-(2-butoxyethoxy)ethyl]4,4'-isopropylidenediphenyl diphosphite.

When present, the phosphite generally constitutes from 0.05% to 5% by weight relative to the weight of the chlorinated polymer, and preferably from 0.1% to 2% by weight.

The compositions according to the invention may also include the usual adjuvants and additives such as phenolic antioxidants, anti-UV agents such as benzophenones, benzotriazoles or sterically hindered amines (typically designated HALS).

The compositions of the invention may be rigid formulations, namely, without any plasticizer, or semi-rigid, namely, with low plasticizer contents, such as for applications in the construction industry or for bottle manufacture. However, the compositions according to the invention may also be employed in plasticized formulations, such as for the manufacture of films for use in agriculture.

The incorporation of the various stabilizers or adjuvants is typically carried out with the chlorinated polymer in powder form.

It is possible, of course, to prepare a mixture of 2 or more of the compounds according to the invention before they are incorporated into the chlorinated polymer.

All of the usual methods for incorporating the various stabilizers or adjuvants in the polymer may be employed. For example, homogenization of the polymeric composition can be carried out on a kneader or roll mill, at a temperature such that the composition becomes fluid, usually ranging from 150° C. to 200° C. in the case of PVC, and for a sufficient period of time, on the order of a few minutes to a few tens of minutes.

The chlorinated polymer compositions, and more particularly PVC, can be converted according to any of the techniques usually employed such as, for example, extrusion, injection, blow-extrusion, calendering or rotational molding.

The compounds of formula (I) may also be employed in other organic polymers.

Thus, they may be employed as UV stabilizers in polyolefins, polystyrenes, polyalkadienes, polyurethanes, polyamides, polyesters, polycarbonates, polysulfones, polyethersulfones, polyetherketones, acrylic polymers, as well as the copolymers and mixtures thereof.

The compounds of formula (I) are employed more particularly in the polyolefins and polyalkadienes such as polypropylene, high density polyethylene, low density polyethylene, linear low density polyethylene, polybutadiene, and the copolymers or mixtures thereof.

From 0.005% to 5% by weight of compound of formula (I) is generally used relative to the weight of the organic polymer, and preferably from 0.01% to 2% by weight.

These organic polymer compositions containing the compounds of formula (I) may additionally contain the additives and stabilizers usually employed, such as antioxidants, light stabilizers, other UV absorbers, metal deactivators, organic phosphites and phosphonites, peroxide-destroyers, fillers, plasticizers, lubricants, emulsifiers, pigments, optical whiteners, flame retardants, antistatics and blowing agents, etc.

In order to further illustrate the present invention and the advantages thereof, the following specific examples are given, it being understood that same are intended only as illustrative and in nowise limitative.

EXAMPLE 1

1(a). Synthesis of the acetoacetate of 4-hydroxyethoxy-2-hydroxybenzpohenone 258 g (1 mole) of 4-hydroxyethoxy-2-hydroxybenzophenone and 1,250 cm$^3$ of dry toluene were charged into a 2,000-cm$^3$ three-necked round bottom flask fitted with a central stirrer, a condenser, a dropping funnel and a side nitrogen delivery tube.

Purging with nitrogen was established such as to place the reaction mass under an inert atmosphere. Heating to 50° C. was applied; at this temperature the reaction mass was homogeneous.

88 g of diketene (1.05 moles) were then introduced over 1 hour, with stirring, while the temperature was maintained between 55° and 60° C. Upon completion of the addition, the temperature was maintained at 60° C. for another 3 hours.

The toluene was then removed under reduced pressure, and the operation was completed at 70° C. at 130 to 260 Pa. The acetoacetate formed set solid on cooling; 341.7 g of an orange-colored crude product, m.p.: 70° C., were obtained. The structure was confirmed by proton NMR and by IR spectrum; the purity was in excess of 95% (chemical yield > 95%).

1(b). Synthesis of 3,5-bis[2-(4-benzoyl-3-hydroxyphenoxy)ethoxycarbonyl]]-2,6-dimethyl-1,4-dihydropyridine 336 g of the product obtained in Example 1(a) (namely, 0.982 mole) and 1,500 cm³ of an isopropanol/-H₂O mixture containing 20% of water by volume were charged into a 4-liter three-necked round bottom flask fitted with a central stirrer, a reflux condenser and a side nitrogen delivery tube; heating to 70°-75° C. was applied such as to obtain a homogeneous solution; 33.3 g of ammonium acetate and 13.75 g of hexamethylenetetramine were then introduced.

Heating to reflux was applied for 2 hours; a yellow precipitate formed quickly during this operation. After permitting the reaction medium to cool, the precipitate was filtered off and was washed 3 times with 200-cm³ portions of an 80/20 isopropanol/H₂O mixture. After drying in a vacuum oven at 50° C., 317.6 g (95.5% yield) of the expected product were thus obtained in the form of a yellow solid having a melting point of 188° C.

Its UV absorption spectrum showed the following characteristics:

$\lambda$ maximum: 238 nm ($\epsilon$ = 30750 1 mol⁻¹ cm⁻¹)
287 nm ($\epsilon$ = 30900 1 mol⁻¹ cm⁻¹)
330 nm ($\epsilon$ = 22500 1 mol⁻¹ cm⁻¹).

EXAMPLES 2 TO 4 AND COMPARATIVE EXAMPLES

Heat Stabilization of PVC

The following base composition A was prepared:

| (i) | PVC powder prepared by bulk or suspension polymerization and marketed under the trademark Lacqvyl SO 71 S (viscosity index according to NF standard T 51013:80) | 1,000 g |
|---|---|---|
| (ii) | Impact modifier (butadiene/styrene/methyl methacrylate copolymer) | 80 g |
| (iii) | Lubricant based on rosin ester (wax E) | 10 g |
| (iv) | Epoxidized soya oil | 40 g |
| (v) | Calcium stearate | 2.5 g |
| (vi) | Zinc stearate | 2.5 g |

After homogenization in a cold fast blender, 5 fractions of the composition A were withdrawn. To each fraction was added a quantity of compound prepared in Example 1(b) (DHP Ex. 1(b)) or of 2,6-dimethyl-3,5-bis(dodecyloxycarbonyl)-1,4-dihydropyridine (prior art DHP) (comparative tests). The quantities by weight per 100 g of PVC are reported in Table I below.

Sheets 1 mm in thickness were prepared using the various compositions thus obtained, and with the unmodified composition A, by milling on a 2-roll mill for 3 min at 180 C.

Using test specimens (approximately 1 cm × 2 cm) cut from these sheets, a heat-aging test was performed in a ventilated oven at 180° C. and the change in the Gardner color was monitored as a function of time.

The Gardner color values measured for different aging periods, and the period of time before complete blackening of the tested samples are reported in Table I.

Examination of the results evidenced that, at equal weight quantity (and therefore a much smaller quantity of 1,4-dihydropyridine functional groups), the compound of the invention (prepared in Example 1(b)) had an efficiency equal to that of a dihydropyridine of the prior art, typically employed.

TABLE I

| TESTS | STABILIZERS | | GARDNER VALUES AS A FUNCTION OF TIME IN MIN | | | | | | | |
|---|---|---|---|---|---|---|---|---|---|---|
| | Nature | Weight in g/100 of PVC | 0 | 7 | 14 | 21 | 30 | 45 | 60 | Black at |
| Control | None | — | 2 | 6 | 7 | 7 | 7 | 8 | 10 | 69 min |
| Example 2 | DHP Ex. 1(b) | 0.10 | 1.5 | 2.5 | 2.5 | 2.5 | 3 | 5 | 9 | 69 min |
| Example 3 | DHP Ex. 1(b) | 0.20 | 1 | 2 | 2 | 2.5 | 3 | 5 | 9 | 69 min |
| Example 4 | DHP Ex. 1(b) | 0.40 | 0.5 | 1.5 | 1.5 | 2 | 2 | 3 | 7 | 67 min |
| Test A1 | prior art DHP | 0.20 | 1 | 2 | 2 | 2.5 | 3 | 5 | 9 | 69 min |
| Test A2 | prior art DHP | 0.40 | 0.5 | 1.5 | 1.5 | 2 | 2 | 3 | 7 | 67 min |

EXAMPLES 5 AND 6 AND COMPARATIVE EXAMPLES

Heat Stabilization of PVC

The following base composition B was prepared:

| (i) | PVC powder prepared by bulk or suspension polymerization and marketed under the trademark Lacqvyl SO 71 S (viscosity index according to NF standard T 51013:80) | 1,000 g |
|---|---|---|
| (ii) | Impact modifier (butadiene/styrene/methyl methacrylate copolymer) | 80 g |
| (iii) | Lubricant based on rosin ester (wax E) | 10 g |
| (iv) | Epoxidized soya oil | 40 g |
| (v) | Calcium stearate | 2.5 g |
| (vi) | Zinc stearate | 2.5 g |

After homogenization in a cold fast blender, 6 fractions of this composition B were withdrawn. To each fraction was added a quantity of stearoylbenzoylmethane (SBM) and optionally a quantity of 2,6-dimethyl-3,5-bis(dodecyloxycarbonyl)-1,4-dihydropyridine (prior art DHP) or of the compound of the invention prepared in Example 1(b) (DHP Ex. 1(b)). The quantities by weight per 100 g of PVC are reported in Table II below.

Sheets 1 mm in thickness were prepared using the various compositions thus obtained, and with the unmodified composition B, by milling on a 2-roll mill for 3 min at 180° C.

Using test specimens (approximately 1 cm × 2 cm) cut from these sheets, a heat-aging test was performed in a ventilated oven at 180° C. and the change in the Gardner color was monitored as a function of time.

The Gardner color values measured for different aging periods, and the period of time before complete blackening of the tested samples are reported in Table II.

TABLE II

| TESTS | STABILIZERS Nature | Weight in g/100 of PVC | GARDNER VALUES AS A FUNCTION OF TIME IN MIN | | | | | | | Black at |
|---|---|---|---|---|---|---|---|---|---|---|
| | | | 0 | 7 | 14 | 21 | 30 | 45 | 60 | |
| Control | None | — | 2 | 6 | 7 | 7 | 7 | 8 | 10 | 69 min |
| Example 5 | SBM | 0.20 | 0 | 0 | 0 | 1 | 2 | 3 | 8 | 65 min |
| | DHP Ex. 1(b) | 0.10 | | | | | | | | |
| Test B1 | SBM | 0.30 | 0 | 0 | 0.5 | 2 | 3.5 | 4 | 9 | 67 min |
| Test B2 | SBM | 0.20 | 0 | 0 | 0 | 1 | 2 | 3.5 | 9 | 64 min |
| | prior art DHP | 0.10 | | | | | | | | |
| Example 6 | SBM | 0.20 | 0 | 0 | 0 | 1 | 1.5 | 3 | 9 | 64 min |
| | DHP Ex. 1(b) | 0.20 | | | | | | | | |
| Test B3 | SBM | 0.40 | 0 | 0 | 0 | 1.5 | 3 | 4 | 9 | 66 min |
| Test B3 | SBM | 0.20 | 0 | 0 | 0 | 1 | 1.5 | 3.5 | 10 | 63 min |
| | prior art DHP | 0.20 | | | | | | | | |

EXAMPLES 7 AND 8 AND COMPARATIVE EXAMPLES

UV Stabilization of PVC

The following base composition C was prepared:

| | | |
|---|---|---|
| (i) | Lacqvyl SO 71 S PVC | 1,000 g |
| (ii) | Butadiene/styrene/methyl methacrylate copolymer | 80 g |
| (iii) | Processing aid (acrylic polymer at high molecular weight) | 5 g |
| (iv) | Hydrogenated castor oil | 13 g |
| (v) | Wax E lubricant | 1.5 g |
| (vi) | Lubricant based on partially saponified propylene glycol montanate (OP wax) | 4.0 g |
| (vii) | Lubricant based on oxidized polyethylene wax (wax AC 316) | 2.0 g |
| (viii) | Calcium stearate | 2.3 g |
| (ix) | Zinc octanoate | 0.9 g |
| (x) | Epoxidized soya oil | 30 g |

After homogenization in a cold mixer, 6 fractions of this composition C were withdrawn. Different stabilizers (reported in Table III below, together with quantities by weight per 100 g of PVC) were added to each fraction.

Sheets 1 mm in thickness were prepared from these different compositions, by milling on a 20-roll mill for 3 min at 180° C.

200-μm films were prepared from these sheets using a press with platens heated to 185° C.

These films were exposed in an accelerated aging enclosure equipped with a fluorescent tube emitting between 290 nm and 400 nm, with a maximum at approximately 360 nm.

The enclosure was maintained at 30° C. and the Gardner color was measured on the various films after an exposure of 192 hours.

The results are reported in Table III below.

The following abbreviations are employed:
SBM = stearoylbenzoylmethane;
prior art DHP: 2,6-dimethyl-3,5-bis(dodecyloxycarbonyl)-2,4-dihydropyridine;
DHP Ex. 1(b): compound of formula (I) prepared in Example 1(b);
Anti UV-E: 2-hydroxy-4-(2-hydroxyethoxy)benzophenone (very widely employed UV stabilizer of the benzophenone type).

TABLE III

| Tests | Stabilizers (in g/100 g PVC) | | Gardner color for 192 h exposure |
|---|---|---|---|
| Example 7 | DHP Ex. 1(b) | 0.25 | 2 |
| Test C1 | prior art DHP | 0.25 | 6 |
| Test C2 | SBM | 0.25 | 7 |
| Example 8 | SBM | 0.125 | |
| | DHP Ex. 1(b) | 0.25 | 2 |
| Test C3 | SBM | 0.125 | 6 |
| | prior art DHP | 0.25 | |
| Test C4 | SBM | 0.125 | 3 |
| | Anti UV-E | 0.25 | |

EXAMPLE 9 AND COMPARATIVE EXAMPLE

The following base composition D was prepared:

| | | |
|---|---|---|
| (i) | Lacqvyl SO 71 S PVC | 1,000 g |
| (ii) | Internal lubricant (mixture of hexadecanol and octadecanol) | 14 g |
| (iii) | Wax E lubricant | 2 g |
| (iv) | Wax OP lubricant | 3 g |
| (v) | Thiotin stabilizer* | 15 g |

(*mixture of 75% by weight of dioctylstanniobis(isooctyl sulfuroacetate), and of 25% by weight of trioctylstannio(isooctyl sulfuroacetate).

and of 25% by weight of trioctylstannio(isooctyl sulfuroacetate).

Following the procedure of Examples 7 and 8, 200-μm films were prepared, containing a UV stabilizer (as reported in Table IV below) or without UV stabilizer (control).

These films were placed in an artificial accelerated aging enclosure, at 58° C., which was equipped with a 40 W type B fluorescent tube emitting between 275 nm and 380 nm, with an intensity maximum at 310 nm.

The change in the optical density of the polyene sequences (containing 10 conjugated double bonds) was monitored in the visible spectrum at a wavelength $\lambda = 447$ nm.

After 750 hours of aging, the values reported in Table IV below were obtained:

TABLE IV

| Tests | Anti-UV stabilizers in g/100 g PVC | Optical density at $\lambda = 447$ nm after 750 hours of aging |
|---|---|---|
| Control | none | 0.40 |
| Example 9 | DHP Ex. 1(b) | 0.15 |
| Test D1 | Anti UVP* | 0.15 |

*Anti UVP = 2-hydroxy-4-octyloxybenzophenone (anti-UV stabilizer of benzophenone type, very widely employed in PVC)

The very marked anti-UV action of the compound of formula (I) prepared in Example 1(b) was noted; this efficiency was equivalent to that of an anti-UV stabilizer of benzophenone type which is very widely employed. Furthermore, this efficiency exists in a composition which is thermally stabilized by a thiotin compound, the photosensitizing action of which is known and considerable.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A heat and light stabilized composition of matter, comprising an organic polymeric matrix, said polymeric matrix having incorporated therein an effective heat/light stabilizing amount of a benzophenone/1,4-dihydropyridine compound having the following formula (I):

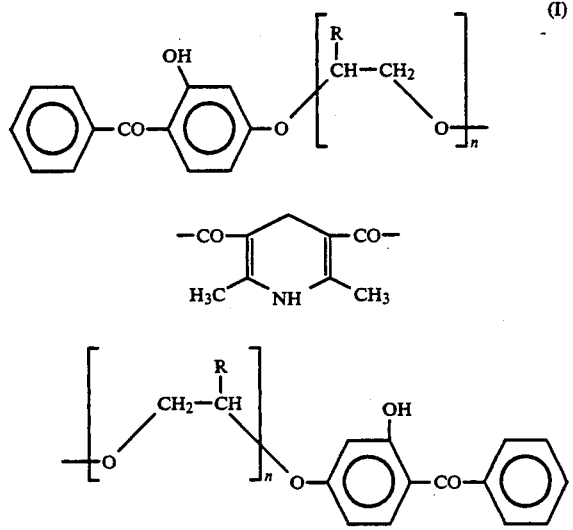

in which n is a number ranging from 1 to 3, and R is a methyl radical or a hydrogen atom.

2. The stable composition as defined by claim 1, said polymeric matrix comprising a halogenated polymer.

3. The stable composition as defined by claim 2, said polymeric matrix comprising a chlorinated polymer.

4. The stable composition as defined by claim 3, said chlorinated polymer comprising polyvinyl chloride or copolymer thereof, polyvinylidene chloride, or mixture thereof.

5. The stable composition as defined by claim 3, further comprising an effective amount of at least one organozinc compound to provide a heat-stabilizing effect and an effective amount of at least one organic calcium, barium, magnesium or strontium compound and/or of a hydrotalcite to provide a heat-stabilizing effect.

6. The stable composition as defined by claim 5, comprising from 0.005% to 5% by weight of said benzophenone/1,4-dihydropyridine compound based on the weight of said chlorinated polymer.

7. The stable composition as defined by claim 6, comprising from 0.01% to 2% by weight of said benzophenone/1,4-dihydropyridine compound.

8. The stable composition as defined by claim 5, comprising from 0.005% to 1% by weight of said at least one organozinc compound and from 0.005% to 5% by weight of said at least one organic calcium, barium, magnesium or strontium compound and/or of said hydrotalcite, both based on the weight of said chlorinated polymer.

9. The stable composition as defined by claim 5, further comprising from 0.005% to 5% by weight of at least one β-diketone, based on the weight of said chlorinated polymer.

10. The stable composition as defined by claim 5, further comprising from 0.005% to 1% by weight of at least one polyol, based on the weight of said chlorinated polymer.

11. The stable composition as defined by claim 5, further comprising from 0.05% to 5% by weight of at least one organic phosphite, based on the weight of said chlorinated polymer.

12. The stable composition as defined by claim 1, said polymeric matrix comprising a polyolefin, polystyrene, polyalkadiene, polyurethane, polyamide, polyester, polycarbonate, polysulfone, polyethersulfone, polyetherketone, acrylic polymer, or copolymer or mixture thereof.

13. The stable composition as defined by claim 12, said polymeric matrix comprising polypropylene, high density polyethylene, low density polyethylene, linear low density polyethylene, polybutadiene, or copolymer or mixture thereof.

14. The stable composition as defined by claim 1, further comprising an effective amount of at least one organotin compound to provide a heat-stabilizing effect.

15. A shaped article comprising the stable composition as defined by claim 1.

* * * * *